United States Patent [19]

Lindberg et al.

[11] 4,098,901
[45] Jul. 4, 1978

[54] TRIFLUOROMETHYL SUBSTITUTED COMPOUNDS HAVING ANTIDEPRESSIVE ACTIVITY

[75] Inventors: Ulf Henrik Anders Lindberg; Svante Bertil Ross, both of Södertälje; Seth Olov Thorberg, Järna; Sven Ove Ögren, Södertälje, all of Sweden

[73] Assignee: Astra Lakemedel Aktiebolag, Sodertalje, Sweden

[21] Appl. No.: 718,569

[22] Filed: Aug. 30, 1976

[30] Foreign Application Priority Data

Sep. 4, 1975 [SE] Sweden .................. 7509814

[51] Int. Cl.² .................. C07C 101/19; A61K 31/22
[52] U.S. Cl. .................. 424/311; 560/173; 560/228
[58] Field of Search .................. 260/482 R; 424/311; 560/173

[56] References Cited

U.S. PATENT DOCUMENTS

| 2,135,641 | 11/1938 | Jacobson | 260/482 |
| 2,480,224 | 8/1949 | Cusic | 260/482 |
| 2,543,764 | 3/1951 | Cusic | 260/482 |
| 2,625,547 | 1/1953 | Lawson | 260/482 |

FOREIGN PATENT DOCUMENTS

| 2,507,429 | 9/1975 | Fed. Rep. of Germany | 260/482 |
| 46-2502 | 1/1971 | Japan | 260/482 |

Primary Examiner—James O. Thomas, Jr.
Assistant Examiner—Michael Shippen
Attorney, Agent, or Firm—Brumbaugh, Graves, Donohue & Raymond

[57] ABSTRACT

A compound of the formula

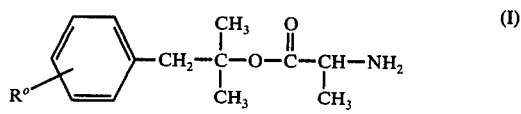

and pharmaceutically acceptable acid addition salts thereof, in which formula the group R° is trifluoromethyl.

Pharmaceutical compositions containing these compounds are useful for treatment of depressive disorders.

9 Claims, No Drawings

TRIFLUOROMETHYL SUBSTITUTED COMPOUNDS HAVING ANTIDEPRESSIVE ACTIVITY

This invention relates to new trifluoromethyl substituted aralkyl esters of amino-acids, and processes for their preparation. This invention also relates to methods for the pharmacological use of these compounds and to pharmaceutical preparations containing such compounds.

An object of this invention is to provide compounds having effect on the central nervous system, especially antidepressive activity, and having a reduced frequency of side effects and increased effectiveness compared to drugs presently used in this area.

A further object of this invention is to provide pharmaceutical preparations containing as active ingredient a compound according to this invention.

Still an object of this invention is to provide methods for the treatment of depressive disorders.

The presently most used compound for controlling depressions is imipramine (Tofranil ®)

$$\text{structure of imipramine with } CH_2CH_2CH_2N[CH_3]_2$$

This compound is both mood elevating and psychomotor activating, but it possesses several disadvantages. It is anticholinergic and causes anticholinergic symptoms such as dryness of the mouth, tremor, tachycardia and sweating. In higher doses it can provoke serious heart arrhythimias and in normal doses it can cause toxic interactions in persons with heart failures. Furthermore, another drawback with treatment with imipramine is the late onset of the antidepressive effect, which effect is observable first after about 3 weeks of treatment.

It has been shown that imipramine has an effect on the action of the transmitter substances in the central nervous system. More specifically, imipramine inhibits the re-uptake mechanism of noradrenaline (NA) and 5-hydroxytryptamine (5-HT). The mood elevation part of the antidepressive action is assumed to be mainly related to the inhibition of 5-HT uptake.

According to the present invention we have found that certain new compounds, which can be described as trifluoromethyl substituted aralkyl esters of amino acids, can be used for inhibiting selectively the central neuronal uptake of 5-hydroxytryptamine. Further the heart toxicities for these new compounds are considerably weaker than those of imipramine.

The new compounds according to the invention can be described by the general formula $$R^o\text{-phenyl-}CH_2-\underset{CH_3}{\underset{|}{C}}(CH_3)-O-\underset{O}{\overset{\|}{C}}-\underset{CH_3}{\underset{|}{CH}}-NH_2 \quad (I)$$

and pharmaceutically acceptable acid addition salts thereof, in which formula the group $R^o$ is trifluoromethyl.

The following two compounds are preferred compounds according to the invention.

2-Aminopropanoic acid 1-(3-trifluoromethylphenyl)-2-methyl-2-propyl ester

2-Aminopropanoic acid 1-(4-trifluoromethylphenyl)-2-methyl-2-propyl ester.

The compounds of the present invention can be prepared by reacting a compound of the formula $$R^o\text{-phenyl-}CH_2-\underset{CH_3}{\underset{|}{C}}(CH_3)-O-\underset{O}{\overset{\|}{C}}-\underset{CH_3}{\underset{|}{CH}}-X \quad (II)$$

with ammonia, in which formula $R^o$ is trifluoromethyl and X is halogen (such as chlorine or bromine) or p-toluenesulphonyloxy.

The intermediate of the formula II is a new compound, and constitutes a further aspect of the invention. Said compound can be prepared by reacting an alcohol of the formula $$R^o\text{-phenyl-}CH_2-C(CH_3)_2-OH$$

with a compound of the formula $$Y-Co-CH(CH_3)X$$

in which formulas $R^o$ and X are defined as above and Y is bromine or chlorine.

The reaction between the compound of the formula II and ammonia is preferably conducted in an inert organic solvent capable of dissolving the reactants. Any suitable pressure and reaction temperature can be used. Preferably, the reaction is carried out under atmospheric or superatmospheric pressure, at a temperature of between $-10°$ to $+100°$ C, preferably between $0°—30°$ C.

The new compounds of this invention may be used therapeutically as the racemic mixtures of $(+)$- and $(-)$-forms, which in the usual case are obtained at the synthesis. They may also be resolved by methods known per se into the corresponding optically active modifications which, likewise, may be used in therapy. If desired, the optically active modification may be prepared by way of direct synthesis, e.g. via an optically active compound of the formula II above.

(b) Pharmaceutical Preparations

In clinical practice the compounds of the present invention will normally be administered orally, rectally or by injection, in the form of pharmaceutical preparations comprising the active ingredient either as a free base or as a pharmaceutically acceptable non-toxic, acid addition salt, e.g. the hydrochloride, hydrobromide, lactate, acetate, phosphate, sulphate, sulphamate, citrate, tartrate, oxalate and the like in association with a pharmaceutically acceptable carrier. Accordingly, terms relating to the novel compounds of this invention whether generically or specifically are intended to include both the free amine base and the acid addition salts of the free base, unless the context in which such terms are used, e.g. in the specific examples would be inconsistent with the broad concept. The carrier may be a solid, semisolid or liquid diluent or capsule. These pharmaceutical preparations, which contain between 0.1 and 95% by weight of the active substance, constitute a further aspect of this invention. Usually the active substance will constitute between 0.5 and 20% by weight for preparations intended for injection and between 2 and 50% by weight for preparations suitable for oral administration.

To produce pharmaceutical preparations containing a compound of the invention in the form of dosage units for oral application the selected compound may be mixed with a solid pulverulent carrier, e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol waxes, and the like, and then compressed to form tablets. If coated tablets are required, the cores, prepared as described above, may be coated with a concentrated sugar solution which may contain, e.g. gum arabic, gelatine, talcum, titanium dioxide, and the like. Alternatively, the tablet can be coated with a lacquer dissolved in a readily volatile organic solvent or mixture or organic solvents. Dyestuffs may be added to these coatings in order to readily distinguish between tablets containing different active substances or different amounts of the active compounds.

For the preparation of soft gelatine capsules (pearl-shaped closed capsules) consisting of gelatine and for example, gylcerol or similar closed capsules, the active substance may be admixed with a vegetable oil. Hard gelatine capsules may contain granulates of the active substance in combination with solid, pulverulent carriers such as lactose, saccharose, sorbitol, mannitol, starches (e.g. potato starch, corn starch or amylopectin), cellulose derivatives or gelatine.

Dosage units for rectal application can be prepared in the form of suppositories comprising the active substance in admixture with a neutral fatty base, or gelatine rectal capsules comprising the active substance in admixture with vegetable oil or paraffin oil.

Liquid preparations for oral application may be in the form of syrups or suspensions, for example, solutions containing from about 0.2% to about 20% by weight of the active substance herein described, the balance being sugar and a mixture of ethanol, water, glycerol, and propyleneglycol. Optionally such liquid preparations may contain colouring agents, flavouring agents, saccharine and carboxymethylcellulose as a thickening agent.

Solutions for parenteral applications by injection can be prepared in the form of an aqueous solution of a water-soluble pharmaceutically acceptable salt of the active substance preferably in a concentration of from about 0.5% to about 10% by weight. These solutions may also contain stabilizing agents and/or buffering agents and may conveniently be provided in various dosage unit ampoules.

Suitable daily doses of the compounds of the invention at therapeutical treatment is 100 to 500 mg at peroral administration and 20 to 100 mg at parenteral administration.

The preferred compound of the invention has the formula

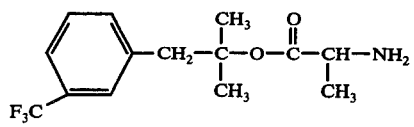

(GEA 820)

Preferably this compound is prepared and used in the form of its hydrochloride salt.

The following example illustrates the preparation of compounds according to the invention.

Preparation of 2-aminopropanoic acid 1-(3-trifluoromethyl-phenyl)-2-methyl-2-propyl ester A solution of 3-trifluoromethylbenzyl chloride (25.0g; 0.128 mole) in ether (130 ml) was added dropwise during 50 minutes to magnesium (3.11 g; 0.128 mole) in a three-necked dry flask equipped with stirrer and reflux condenser. The spontaneous reflux was allowed to continue for another half an hour. The solution was cooled and acetone (7.45; 0.128 mole) was added dropwise (8 minutes) and the solution heated to reflux for three hours. After cooling the reaction mixture was poured out on ice (100 ml) and concentrated hydrochloric acid (11 ml). The phases were separated. The organic phase was washed with water, dried ($Na_2SO_4$) and evaporated in vacuum. The residual oil was fractioned affording 1-(3-trifluoromethylphenyl)-2-methyl-2-propanol. (B.p. 63°–64° C/1.0 mm Hg, M.p. 55°–56° C recryst. from petroleum ether.) Yield: 73%; 20.3 g.

The substituted propanol above (15.0 g; 0.069 mole) was mixed with dimethylaniline (9.32 g; 0.077 mole) and dichloromethane (50 ml). The solution was cooled and 2-bromopropionylbromide (22.2 g; 0.103 mole) was added dropwise during one hour. Stirring at room temperature was continued over night. Water (200 ml) was added to the reaction mixture and the phases were separated. After washing with a 2 N sodium hydrogen carbonate solution the organic phase was evaporated in vacuum. The residual oil was diluted with ether (200 ml) washed three times with 0.1 N sulphuric acid and water. The ether solution was dried ($Na_2SO_4$) and evaporated in vaccum. The residual oil afforded 2-bromopropanoic acid 1-(3-trifluoromethylphenyl)-2-methyl-2-propyl ester (21.0 g; 87%).

The bromoester (21.0 g; 0.059 mole) obtained above was dissolved in ethanol (600 ml) and wash cooled to 0° C. The solution was saturated with ammonia (4 hours). Stirring was continued at room temperature for 52 hours with two further saturations with ammonia. The solvent was removed under vaccum. The residual oil was dissolved in 0.2 N hydrochloric acid and washed with ether. The acidic phase was made alkaline by addition of 2 N sodium hydroxide to pH 9.0. The alkaline phase was extracted twice with ether. The organic layer was washed with water, dried ($Na_2SO_4$) and evaporated in vacuum. From the basis oily residue the hydrochloride was prepared. Recrystallization from aceton afforded 2-aminopropanoic acid 1-(3-trifluoromethylphenyl)-2-methyl-2-propyl-ester hydrochloride (m.p.: 140°–141° C; 12.70 g, 66% yield).

PHARMACOLOGICAL METHODS

A. Biochemical tests

1. Inhibition of the uptake of carbon-14 5-HT and tritiated noradrenaline in vitro and in vivo The method is described by Rose, Renyi and Ogren in European Journal of Pharmacology 17 (1972), 107-112. Tricyclic antidepressant drugs of type imipramine added in vitro or given in vivo to mice decrease the uptake of Hu 14C-5-HT and hu 3H-Na in vitro. In the in vitro experiments different concentrations of the test compound were added to the incubation medium. In the in vivo experiments different doses of the test drug were administered intraperitoneally half an hour before the animals were killed. The incubation performance was the same in the two types of experiments, i.e. the midbrain was taken out and sliced and incubated in a mixture consisting of, per 100 mg of brain slices, 0.2 n-mole of hu 14C-5-HT, 0.2 n-mole of hu 3H-NA and 11 umole of glucose in 2 ml of Krebs-Henseleit buffer, pH 7.4. The incubation time was 5 minutes. The radioactive amines taken up in the slices were dissolved in Soluene-350 ® (Packard) and the amounts were determined with the double labelling technique by liquid scintillation. The concentration or dose producing 50 percent decrease of the active uptake ($ED_{50}$) was determined graphically from dose-response curves. Active uptake is defined as that part of the radioactive uptake which is inhibited by a high concentration of cocaine. All doses were given at least to four animals.

The result from the above described tests are summarized in the following Table. The code number GEA 820 represent the compound 2-aminopropanoic acid 1-(3-trifluoromethylphenyl)-2-methyl-2-propyl ester hydrochloride, i.e a compound according to the invention.

Table

| | Inhibition (50%) of uptake | | | |
|---|---|---|---|---|
| | in vitro | | in vivo | |
| | 5-HT[1] | NA[2] | 5-HT[1] | NA[2] |
| Compound | (ug/ml) | | (mg/kg i.p.) | |
| GEA 820 | 0.5 | >10 | 30 | >40 |
| Imipramine | 0.1 | 0.06 | 24 | 6 |

[1]5-HT = 5-hydroxytryptamine, $1 \times 10^{-7}M$
[2]NA = 1-noradrenaline, $1 \times 10^{-7}M$
i.p. = intraperitoneal administration

ELVALUTION OF THE RESULTS OBTAINED IN THE PHARMACOLOGICAL TESTS

The compounds of the invention block the uptake of 5-hydroxy-tryptamine in brain slices in vitro and in vivo but do not inhibit the uptake of noradrenaline.

These results indicate that the new compounds are much more selective than imipramine in inhibiting the uptake of 5-hydroxy-tryptamine.

PHARMACEUTICAL COMPOSITIONS

The following examples illustrates the preparation of pharmaceutical compositions according to the invention. For the preparation of tablets the following compositions were made

| a) | 2-Aminopropanoic acid 1-(3-trifluoro-methylphenyl)-2-methyl-2-propyl ester hydrochloride (GEA 820) | 50 g |
|---|---|---|
| | Lactose | 85 g |
| | Potatoe starch | 40 g |
| | Polyvinylpyrrolidone | 5 g |
| | Cellulose Avicel | 18 g |
| | Magnesium stearate | 2 g |
| b) | 2-Aminopropanoic acid 1-(3-trifluoro-methylphenyl)-2-methyl-2-propyl ester hydrochloride (GEA 820) | 100 g |
| | Lactose | 90 g |
| | Potatoe starch | 50 g |
| | Polyvinylpyrrolidone | 5 g |
| | Cellulose Avicel | 23 g |
| | Magnesium stearate | 2 g |

From the above compositions 1000 tablets were made, containing 50 mg and 100 mg of active substance, respectively. If desired, the obtained tablets can be film coated with e.g. methyl cellulose in an organic solvent.

We claim:

1. A compound of the general formula

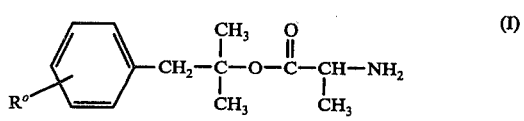

or a pharmaceutically acceptable acid addition salt thereof, in which formula the group $R^o$ is trifluoromethyl.

2. A compound according to claim 1 of the formula

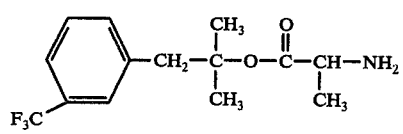

or a pharmaceutically acceptable acid addition salt thereof.

3. A compound according to claim 1 of the formula

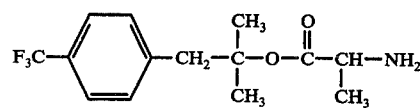

or a pharmaceutically acceptable acid addition salt thereof.

4. A pharmaceutical composition comprising as active ingredient between 0.1 and 95% by weight of a compound as claimed in claim 1, together with a pharmaceutically acceptable carrier, for use in the treatment of depressive disorders related to neuronal uptake of 5-hydroxytryptamine.

5. A pharmaceutical composition comprising as active ingredient between 0.1 and 95% by weight of a compound as claimed in claim 2, together with a pharmaceutically acceptable carrier, for use in the treatment of depressive disorders related to neuronal uptake of 5-hydroxytryptamine.

6. A pharmaceutical composition comprising as active ingredient between 0.1 and 95% by weight of a compound as claimed in claim 3, together with a pharmaceutically acceptable carrier, for use in the treatment of depressive disorders related to neuronal uptake of 5-hydroxytryptamine.

7. A method for the treatment of depressive disorders related to neuronal uptake of 5-hydroxytryptamine, the method comprising administration to a host in need of such treatment of a therapeutically effective amount of a compound as claimed in claim 1.

8. A method for the treatment of depressive disorders related to neuronal uptake of 5-hydroxytryptamine, the method comprising administration to a host in need of such treatment of a therapeutically effective amount of a compound as claimed in claim 2.

9. A method for the treatment of depressive disorders related to neuronal uptake of 5-hydroxytryptamine, the method comprising administration to a host in need of such treatment of a therapeutically effective amount of a compound as claimed in claim 3.

* * * * *